United States Patent [19]

Koppel et al.

[11] Patent Number: 5,734,090
[45] Date of Patent: Mar. 31, 1998

[54] METHOD AND APPARATUS FOR SONIC BREATH DETERMINATION

[75] Inventors: Ronald Koppel, Huntington; Edwin Kirchmeier, Hauppauge, both of N.Y.

[73] Assignee: Alcohol Sensors International, Ltd., Islandia, N.Y.

[21] Appl. No.: 624,797

[22] Filed: Mar. 27, 1996

[51] Int. Cl.$^6$ .................................................. A61B 5/00
[52] U.S. Cl. ................................................ 73/23.3; 340/576
[58] Field of Search ........................... 128/716, 725; 340/576; 73/23.3

[56] References Cited

U.S. PATENT DOCUMENTS

| | | | |
|---|---|---|---|
| 3,809,067 | 5/1974 | Hoppesch | 340/576 |
| 3,824,537 | 7/1974 | Albertson | 340/576 |
| 3,990,435 | 11/1976 | Murphy | 128/716 |
| 4,809,810 | 3/1989 | Elfman et al. | 340/576 |
| 5,143,078 | 9/1992 | Mather et al. | 128/716 |

*Primary Examiner*—George M. Dombroske
*Assistant Examiner*—Ronald L. Biegel
*Attorney, Agent, or Firm*—Schweitzer Cornman Gross & Bondell LLP

[57] ABSTRACT

A method and apparatus for verifying an expiratory breath flow utilizes the sonic characteristics of a standardized breath as a reference. A breath sample is analyzed for the presence and absence of predetermined audio frequency components generated by the expiratory process. Breach sample validity is based upon a match between both the required and missing components. The length of time that the required components are present can further be used to validate the sample.

13 Claims, 2 Drawing Sheets

$-V_H$
$0$ $T \rightarrow$

METHOD AND APPARATUS FOR SONIC BREATH DETERMINATION

The present invention relates to a new and improved method and apparatus for the monitoring and measuring of an air flow, and in particular an expiratory air flow generated by a human breath.

BACKGROUND OF THE INVENTION

The constituents of a human breath are reflective of many physiological characteristics of the body. Accordingly, the measuring of such constituents may have applicability in many areas. As an example, it is well established that the degree of alcohol in the breath is an accurate determinant of the alcohol level in the blood. Such a blood alcohol level is itself a universally used determinant for "driving while intoxicated" and "driving while impaired" statutes.

As the use of breath-derived data increases, the concerns that the data derived therefrom are accurate similarly expands. Such concerns may be divided into two general areas. First, there must be assurances that the breath sample which is being monitored and measured is full and complete. In alcohol sensing systems, for example, it is imperative that the breath sample comprise deep alveolar air, a condition that occurs when an expiratory breath substantially exhausts the lungs. The second concern is that the sample being monitored is, in fact, a breath sample as opposed to an artificial breath. Particularly when breath samples are taken in an unsupervised environment, such a concern can be of greatest importance.

There have been many methodologies developed in attempts to insure that a measured breath sample meets the foregoing requirements. Such methodologies have included measurements of sample temperature and humidity, as well as velocity and pressure profiles. In general, however, such methodologies are subject to shortcomings. Often they require multiple sensors, and relatively complex circuitry and/or systems for processing the sensor's output. In addition, subject to subject variation in breath characteristics can often lead to inaccurate results.

It is accordingly a purpose of the present invention to provide a method and apparatus for the determination and measurement of a human expiratory breath.

Another purpose of the present invention is to provide such a method and apparatus through a system which requires a minimum number of sensing devices.

Still a further purpose of the present invention is to provide such a method and apparatus which exhibits a strong resistance to subject to subject variations, and which may be implemented in a simple and efficient manner.

BRIEF DESCRIPTION OF THE INVENTION

In accordance with the above and further objects and purposes, a breath sensor in accordance with the present invention incorporates a system and methodology for measuring sonic characteristics of an input breath stream. It has been determined that certain tonal characteristics of a deep expiratory human breath do not substantially deviate, over at least a major portion of the adult population, and thus the pressure of such characteristics can be used to validate a breath sample. The identification of such particular tonal characteristics of a human breath, preferably coupled with a further analysis to determine whether other, non-breath-related frequencies are present, a highly accurate confirmation of a valid breath can be performed. In such a coupled analysis, a breath sample is acknowledged based upon the presence of the breath-related frequencies simultaneous with the non-presence of the non-breath-related frequencies. By further coupling such frequency analysis with a breath time determination, preferably based upon the duration of a valid frequency signature, a highly accurate breath sample profile can be obtained.

DETAILED DESCRIPTION OF THE INVENTION

It has been found that, when the human lips are formed into a large "O"-shape and a deep exhalation is made without the introduction of vocalized or intonaled sounds, the exhaled air passing through the mouth has a complex frequency spectrum produced by the resonance conditions formed by the mouth cavity. Initial investigations have indicated that this frequency spectrum is unique to the human mouth when the mouth is formed as stated. A particular portion of the overall spectrum is centered at approximately 500 Hz and has a bandwidth of approximately 200 Hz. The volume of air passing through the mouth per unit time is established by the size and shape of the mouth opening and has a direct correlation to the sound pressure level of the exiting air stream. In general, the variations in mouth size does not vary significantly; thus monitoring the sound pressure level over the duration of the expiratory flow, an approximate total flow volume can be determined by reference to duration without adjustment for mouth size.

Figure 1:
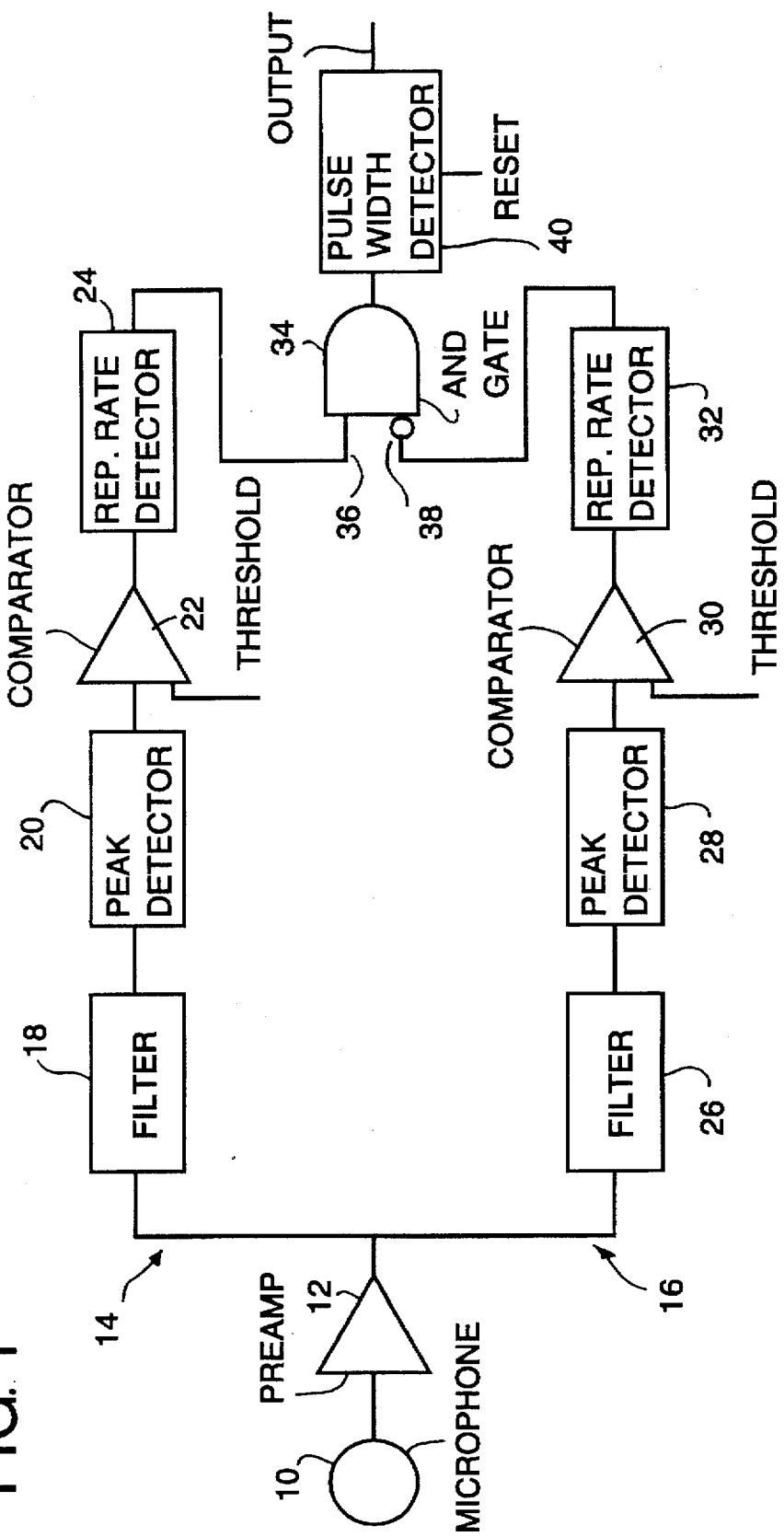
FIG. 1 is a block diagram of an apparatus embodying the present invention.

As shown in FIG. 1, a condenser microphone 10 having a broad frequency response, typically 10–20,000 Hz, is provided to monitor the sonic characteristics of an airflow sample. The microphone may be mounted within a breath collection passageway (not shown) to direct the airflow across the microphone. Preferably, the passageway should provide minimal resistance to the air flow passing therethrough and should be of a material chosen to avoid the creation of resonances or otherwise meaningfully distort the sonic frequency spectrum associated with the air flow. The microphone is coupled to a preamplifier 12. The output of the preamplifier, which is preferably a broad band, constant gain type as known in the art, is divided into two parallel processing paths 14 and 16.

First processing path 14 includes filter 18 chosen to be responsive to a frequency characteristic of the breath. Preferably, a bandpass filter is employed, and may have a center frequency of approximately 500 Hz and a bandwidth of approximately 100 Hz. Such a filter can be easily constructed by those skilled in the art. The output of the filter 18 is passed to peak detector 20, preferably having a time constant chosen to be several periods of the center frequency of the passband filter. The output of the detector 20 is in turn passed to comparator 22 having its threshold set to correspond to a desired sound pressure level, which may be on the order of +6 to 8 microbar. The output of the comparator is then fed to a digital pulse repetition rate detector 24 which is set to generate an output when an input pulse train extends over at least a period corresponding to several periods of the center frequency for the passband filter.

The second processing path 16 similarly includes a filter, which may be a passband filter 26, followed by peak detector 28, comparator 30, and repetition rate detector 32. The second filter 26 is chosen to be responsive to a frequency or frequency bandwidth typically not associated with a valid breath sample, and thus is used as a check against the creation of a breath sample by artificial means. A filter having a center frequency of approximately 6000 Hz, and a bandwidth of approximately 1200 Hz, has been found to yield successful results. Such a bandwidth is typically found in mechanical devices capable of generating an air flow which also includes frequency components lying in the range of 500 Hz.

The outputs of the repetition rate detectors 24 and 32 are combined through a logical And gate 34. The gate 34 is so configured that an output is generated only when there is a signal on its first input 36 and no signal on its second input line 38. Thus, an output is generated only when a low-frequency component, and not a high-frequency component is present in the airflow (or breath) sample. The output of And gate 34 is fed to digital pulse width detector 40. This detector generates an output only when the input thereto is greater than a particular duration and is of particular importance when the breath sample must correspond to a particular degree of lung evacuation. A duration of three seconds, for example, may be chosen in combination with an alcohol-sensing system to insure that the monitored breath flow is sufficiently long to insure that firstly an adequate sample is developed, and secondly that the breath includes deep alveolar air, to insure a valid alcohol level sampling.

Figure 2A:
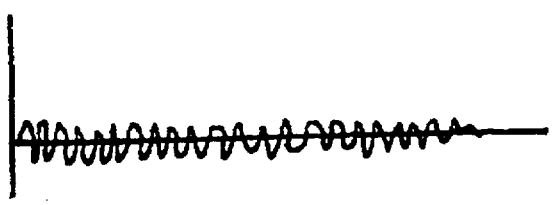
FIGS. 2A through 2I are representative of electrical waveforms present at particular locations in the apparatus set forth in FIG. 1.
Figure 2B:
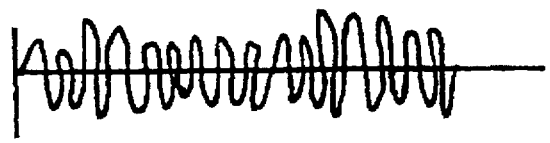
Figure 2C:
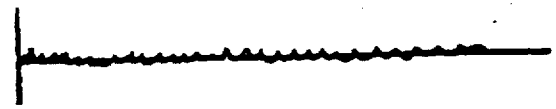

As shown in FIG. 2A, the output of microphone 10 is a complex waveform representing the entire spectrum of audio frequencies associated with the air sample passing the microphone. When the air sample comprises a human expiratory breath generated in accordance with the present invention, the frequency spectrum includes a set of frequencies associated with the breath which do not substantially vary from individual to individual. After passing through passband filter 18, a signal represented by FIG. 2B is developed. This signal is a composite of the audio frequencies present in the breath sample across the passband of the filter and it is this frequency spectrum which is indicative of a proper breath sample. With the assumption that a proper breath sample exists, FIG. 2C presents the output of second passband filter 26. Other than a small noise component, this figure band indicates that no frequency components associated with a mechanically-created signal are present.

Figure 2D:
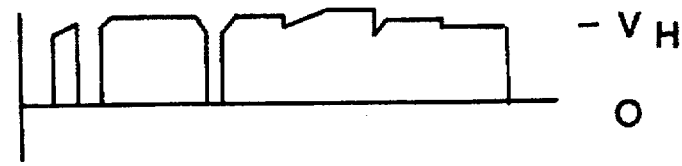
Figure 2E:
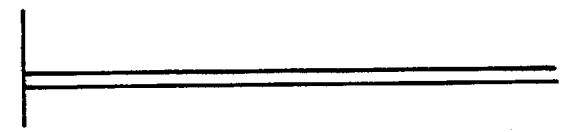

After passing through first peak detector 20, the signal in the first processing path 14 yields an output signal as depicted in FIG. 2D. The magnitude of the output signal is at or exceeds $V_H$ during such periods of time that the amplitude of the passband waveform output from the passband filter exceeds the set reference level. Because the output of second bandpass filter 26 in the second processing path 16 is essentially zero, the output of second peak detector 28, as shown in FIG. 2E, is essentially zero.

Figure 2F:
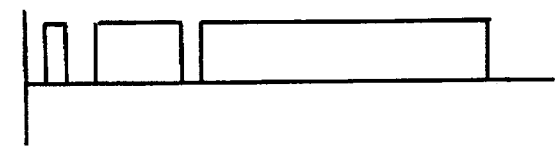
Figure 2G:

After passing through comparator 22, the output signal for the first processing path is as shown in FIG. 2F. A series constant amplitude pulses are generated, the duration of the pulses corresponding to the length of time that the output of peak detector 20 is at or above the reference $V_H$ level. The output of second comparator 30, shown in FIG. 2G, is essentially zero, save for random pulses resulting from noise, and the like.

Figure 2H:
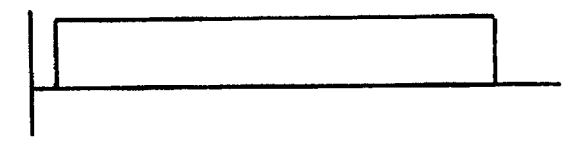

The repetition rate detectors 24 and 32 serve to analyze the pulse trains generated by the comparators, and are adjusted to provide an output signal when sufficient pulses appear that their respective inputs exist over a given period of time, indicating the continued presence of the associated frequency component in the input signal. Typically, the repetition rate is chosen to be several periods of the center frequency of the associated passband filter to be responsive to continuity of the sensed frequency spectrum while avoiding a sensitivity to possible instantaneous signal variations which may accompany a valid breath. As shown in FIG. 2H, the output of repetition rate detector 24 is shown as generating a continuous output, acknowledging the generally continuous nature of the frequency spectrum components in the microphone output representing a valid breath sample.

Second peak repetition rate detector 32, which is part of the second processing path 16 adapted to identify non-conforming frequency components, is set somewhat differently. In particular, it is preferred that this repetition rate detector generate an output when far fewer pulses are received. This increases the sensitivity of the system to non-complying frequencies processed by the second path and thus improves the overall accuracy of the system. While the second repetition rate detector is set not to generate an output if isolated pulses, such as shown in FIG. 2G, are present, any statistically significant group of pulses would result in an output being generated.

Figure 2I:
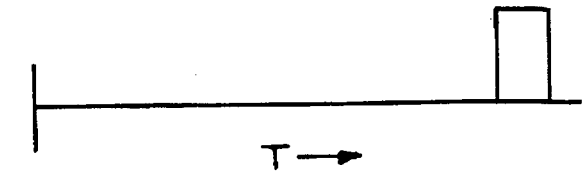

The output of And gate 34 is depicted in FIG. 2I. That output, which is simply a control pulse representing a logical "one", is generated when the output of the gate is high for a predetermined length of time, thus signifying the presence of breath-certifying frequencies, and the absence of disqualifying frequencies, over that period of time, which is typically chosen to represent a full breath. The output pulse of FIG. 2I may serve as a trigger for subsequent processing circuitry and confirms that a valid breath sample has been received. The generation of such a pulse can also trigger appropriate logic circuitry which generates a re-set pulse to the pulse width detector, resetting it for a subsequent analysis.

It is to be recognized that additional, parallel processing paths for other frequency components of an input breath may be utilized as part of the present invention. These processing paths may correspond to other discreet frequencies or frequency bands present in a valid breath, whereby their presence is required to generate a positive output, or may constitute other frequencies or frequency bands not associated with a human breath, whose presence would indicate the existence of a non-valid breath. Additional pathways for both qualifying and disqualifying components may be utilized as desired, And gate 34 summing the pulse signals representing the presence (or the absence) of such components as required.

We claim:

1. An apparatus for identifying a human breath, comprising:
    a microphone;
    at least one first audio frequency filter means coupled to said microphone having a passband corresponding to at least one frequency associated with a particular form of expiratory breath;
    at least one second audio frequency filter means coupled to said microphone having a passband corresponding to at least one frequency not associated with said particular form of expiratory breath;
    means coupled to said first audio filter means for generating an output signal for a duration that said at least one frequency associated with the breath is present;

means coupled to said second audio filter means for generating an output signal for a duration that said at least one frequency not associated with said breath is present; and means coupled to said generating means for generating a second output for so long as said first generating means has an output and said second generating means does not have an output.

2. The apparatus of claim 1, wherein said first and second audio frequency filter means comprise bandpass filters.

3. The apparatus of claim 2, wherein said first bandpass filter has a center frequency of about 500 Hz and a bandwidth of about 100 Hz.

4. The apparatus of claim 2 or claim 3, wherein said second bandpass filter has a center frequency of about 6000 Hz and a bandwidth of about 1200 Hz.

5. The apparatus of claim 2, wherein said means coupled to said first audio filter means for generating an output signal comprise a peak detector, a comparator, and a pulse repetition rate detector.

6. The apparatus of claim 5, wherein said means coupled to said second audio filter means for generating an output signal comprise a peak detector, a comparator, and a pulse repetition rate detector.

7. The apparatus of claim 6, wherein said means for generating a second output comprise an And gate coupled to said pulse repetition rate detectors.

8. A method for identifying an air flow as a human expiratory breath by the analysis of sonic characteristics, comprising the steps of:

identifying a first frequency band present in the frequency spectrum of a human expiratory breath generated by a defined mouth shape and diaphragm action, and a second frequency band not present in said frequency spectrum;

sensing the presence of said first and second frequency bands in connection with the air flow to be analyzed; and generating an output signal signifying a valid breath if said first frequency band is present, and said second frequency band is not present, for an airflow duration representing a valid breath.

9. An apparatus for identifying an airflow as a human breath, comprising:

means for sensing the presence in the airflow of at least one audio frequency component generated by a human breath of a predetermined form;

means for sensing the presence in the airflow of at least one other audio frequency component not generated by the predetermined form breath;

means for measuring the volumetric flow rate of the airflow associated with the presence of at least one audio frequency component generated by the predetermined form breath; and means for generating an output confirming the airflow as a human breath if said at least one audio frequency is present, said at least one other frequency component is not present, and said volumetric flow rate exceeds a fixed level.

10. The apparatus of claim 9, wherein said output-generating means comprises means for generating an output when said at least one audio frequency is present, said at least one other frequency component is not present, and said volumetric flow rate exceeds a fixed level for a predetermined length of time.

11. The apparatus of claim 9 or claim 10, wherein said means for measuring the volumetric flow rate comprises means for measuring the sound pressure of said at least one audio frequency component generated by the predetermined breath form.

12. The apparatus of claim 11, wherein said output-generating means comprises means for comparing the sound pressure of said at least one audio frequency component to a reference value.

13. The apparatus of claim 12, wherein said reference value is between about 6 and 8 microbar.

* * * * *